United States Patent [19]

Wilson et al.

[11] Patent Number: 6,096,322

[45] Date of Patent: Aug. 1, 2000

[54] **PATHOGENICITY AND PROTECTIVE ATTRIBUTES OF MAJOR CLONES OF *ESCHERICHIA COLI* RECOVERED FROM CHICKENS DURING PROCESSING**

[75] Inventors: Richard A. Wilson, Boalsburg; Thomas Whittam, State College, both of Pa.; Vivek Kapur, St. Anthony, Minn.

[73] Assignee: The Penn State Research Foundation, University Park, Pa.

[21] Appl. No.: 08/880,844

[22] Filed: Jun. 23, 1997

Related U.S. Application Data

[63] Continuation-in-part of application No. 08/076,995, Jun. 15, 1993, Pat. No. 5,641,491.

[51] Int. Cl.⁷ ........................ A61K 39/108; G01N 33/569
[52] U.S. Cl. ........................ 424/257.1; 435/7.2; 435/7.32; 435/7.37
[58] Field of Search .................... 435/7.2, 7.32, 435/7.37; 424/257.1

[56] References Cited

U.S. PATENT DOCUMENTS 4,404,186  9/1983  Ron .

OTHER PUBLICATIONS

White et al., *Microbiol Pathogen.*, vol. 14, pp. 399–409, May, 1993.

Møller et al., *J. Clin. Microbio.*, vol. 30, pp. 623–672, Mar., 1992.

Kapur et al., *Infect. Immun.*, vol. 60, pp. 1687–1691, Apr., 1992.

Whittam et al., *Infect. Immun.*, vol. 56, pp. 2458–2466, 1988.

*Primary Examiner*—Gary L. Kunz
*Assistant Examiner*—Stephen Gucker
*Attorney, Agent, or Firm*—Thomas J. Monahan

[57] ABSTRACT

New methods and compositions suitable for the vaccination of poultry against pathogenic *Escherichia coli* are presented. The invention uses the clonal structure of bacterial populations in order to successfully vaccinate against such poultry pathogens by selecting out closely related non-pathogenic organisms. Live *E. coli* are used to effect immunization.

7 Claims, 3 Drawing Sheets

PATHOGENICITY AND PROTECTIVE ATTRIBUTES OF MAJOR CLONES OF *ESCHERICHIA COLI* RECOVERED FROM CHICKENS DURING PROCESSING

This application is a continuation-in-part of U.S. patent application Ser. No. 08/076,995 filed Jun. 15, 1993, now U.S. Pat. No. 5,641,491.

BACKGROUND OF THE INVENTION

The present invention relates to the field of veterinary medicine, specifically to materials and methods for the immunization of poultry against *Escherichia coli* infections.

By way of background, *Escherichia coli* infections in poultry represent a variety of clinical conditions including airsacculitis, pericarditis, and perihepatitis. Collectively, these conditions are a major cause of economic loss to the poultry industry [Gross, W. B., Colibacillosis in *Diseases of Poultry*, 9th ed., Calnek, B. W. et al., eds., Iowa State University Press, P. 138, 1991]. The extent of the economic loss due to diseases caused by *E. coli* in poultry, however, is often underestimated because a substantial number of birds are condemned at processing plants. For instance, more than 42 million young chickens were condemned due to airsacculitis or septicemia in 1988 [Anonymous, Federal meat and poultry inspection FY89 Statistical summary annual. July 1990 (P). Congressional Information Service, Washington D.C.]. In 1989, the number of young chickens condemned was nearly 40 million accounting for approximately 70% of all condemnations.

Both airsacculitis and septicemia are conditions that can be caused by *E. coli* infections, and not surprisingly, *E. coli* can be readily isolated from tissues of a large percentage of birds that are condemned in processing plants [Kapur, V. et al. Characterization and Clonal Analysis of *Escherichia coli* Isolated from Poultry During Processing, Manuscript in preparation]. These isolates fell into several previously described genetic clusters of organisms isolated from clinical cases of avian colibacillosis, swollen head syndrome, and from apparently healthy birds [Whittam, T. S., et al. *Infect. Immun.* 56:2458–2466, 1988; White, D. G., et al. *Infect. Immun.* 58:3613–3620, 1990], as well as into some clonal groups not previously described. Significantly, none of the isolates recovered from processing plants belonged to clone cluster A1, a majority of whose isolates were recovered from the heart, air sac, or liver, and is thought to be a specialized avian cluster containing pathogenic *E. coli*. In addition, nearly a third of the isolates recovered from birds condemned at processing plants were previously discovered to belong to a clonal group (cluster C) that contains mostly low virulence strains. These results, along with serotypic analysis of *E. coli* isolates from processing plants have indicated that the bacterial strains associated with condemnation at processing plants do not necessarily represent the same population of isolates associated with clinical disease.

As emphasis has previously been placed on routinely collecting and characterizing isolates from clinically ailing birds, there is little information available on the pathogenic attributes of major clones associated with condemned birds. In this study, we assessed the degree of virulence of isolates representing the major clones and clonal groups recovered from birds condemned at processing, and experimentally determined if isolates were able to protect birds against challenge with closely related strains.

SUMMARY OF THE INVENTION

In accordance with the present invention, new materials and methods for the vaccination of poultry against pathogenic *Escherichia coli* infections are presented. Various *E. coli* isolates were recovered from chickens at poultry plants and evaluated. After administration with certain live strains of *E. coli*, immunization was effected.

OBJECTS OF THE INVENTION

An object of this invention is to provide a method for immunization of poultry against *Escherichia coli* infections.

It is also an object of this invention to provide certain *E. coli* isolates which may be administered live to poultry and which impart immunity against pathogenic *E. coli*.

This and other objects and advantages of the invention over the prior art and a better understanding of its use will be readily apparent from the following description and are particularly delineated in the appended claims of the invention.

MATERIALS AND METHODS

Bacterial isolates. A total of 33 *E. coli* isolates recovered from 28 broiler chickens during processing at two federally inspected poultry plants in Pennsylvania were evaluated during the course of this study (Table 1). A sample of *E coli* strain 364 was deposited Oct. 8, 1996, with the American Type Culture Collection, 12301 Parklawn Drive, Rockville, Md. 20852 ("ATCC"), and the deposit was assigned accession number 98222, hereinafter referred to as "ATCC Accession No. 98222."

TABLE 1

Properties associated with 33 isolates recovered from processing plants used in challenge studies

| Isolate Number | Bird Number | Origin | | | |
|---|---|---|---|---|---|
| | | Disease[a] | Organ | Plant | Site[b] |
| 266 | 26 | AS | Liver | 1 | Out |
| 270 | 27 | AS | Liver | 1 | Out |
| 281 | 29 | AS | Lung | 1 | In |
| 289 | 31 | Sep | Lung | 1 | In |
| 291 | 32 | Sep | Lung | 1 | Out |
| 298 | 34 | Sep | Liver | 1 | Out |
| 302 | 35 | Sep | Lung | 1 | Out |
| 306 | 36 | Sep | Liver | 1 | Out |
| 309 | 36 | Sep | Lung | 1 | In |
| 313 | 37 | Sep | Lung | 1 | In |

TABLE 1-continued

Properties associated with 33 isolates recovered from processing plants used in challenge studies

| Isolate Number | Bird Number | Origin | | | |
|---|---|---|---|---|---|
| | | Disease[a] | Organ | Plant | Site[b] |
| 323 | 40 | AS | Lung | 1 | Out |
| 329 | 41 | Sep | Lung | 1 | In |
| 331 | 42 | Sep | Lung | 1 | Out |
| 333 | 42 | Sep | Lung | 1 | In |
| 351 | 47 | Sep | Lung | 1 | In |
| 364 | 51 | AS | Liver | 1 | Out |
| 368 | 52 | Sep | Liver | 1 | Out |
| 393 | 58 | N | Lung | 1 | In |
| 397 | 59 | N | Lung | 1 | In |
| 403 | 61 | N | Lung | 1 | Out |
| 417 | 64 | N | Lung | 1 | In |
| 418 | 65 | N | Liver | 1 | Out |
| 433 | 69 | AS | Liver | 2 | Out |
| 436 | 70 | N | Lung | 2 | Out |
| 463 | 77 | AS | Liver | 2 | In |
| 464 | 77 | AS | Lung | 2 | In |
| 468 | 78 | Sep | Lung | 2 | In |
| 470 | 79 | AS | Lung | 2 | Out |
| 475 | 81 | Sep | Liver | 2 | Out |
| 477 | 81 | Sep | Liver | 2 | In |
| 478 | 81 | Sep | Lung | 2 | In |
| 489 | 84 | AS | Liver | 2 | In |
| 503 | 88 | Sep | Liver | 2 | Out |

Figure 1:
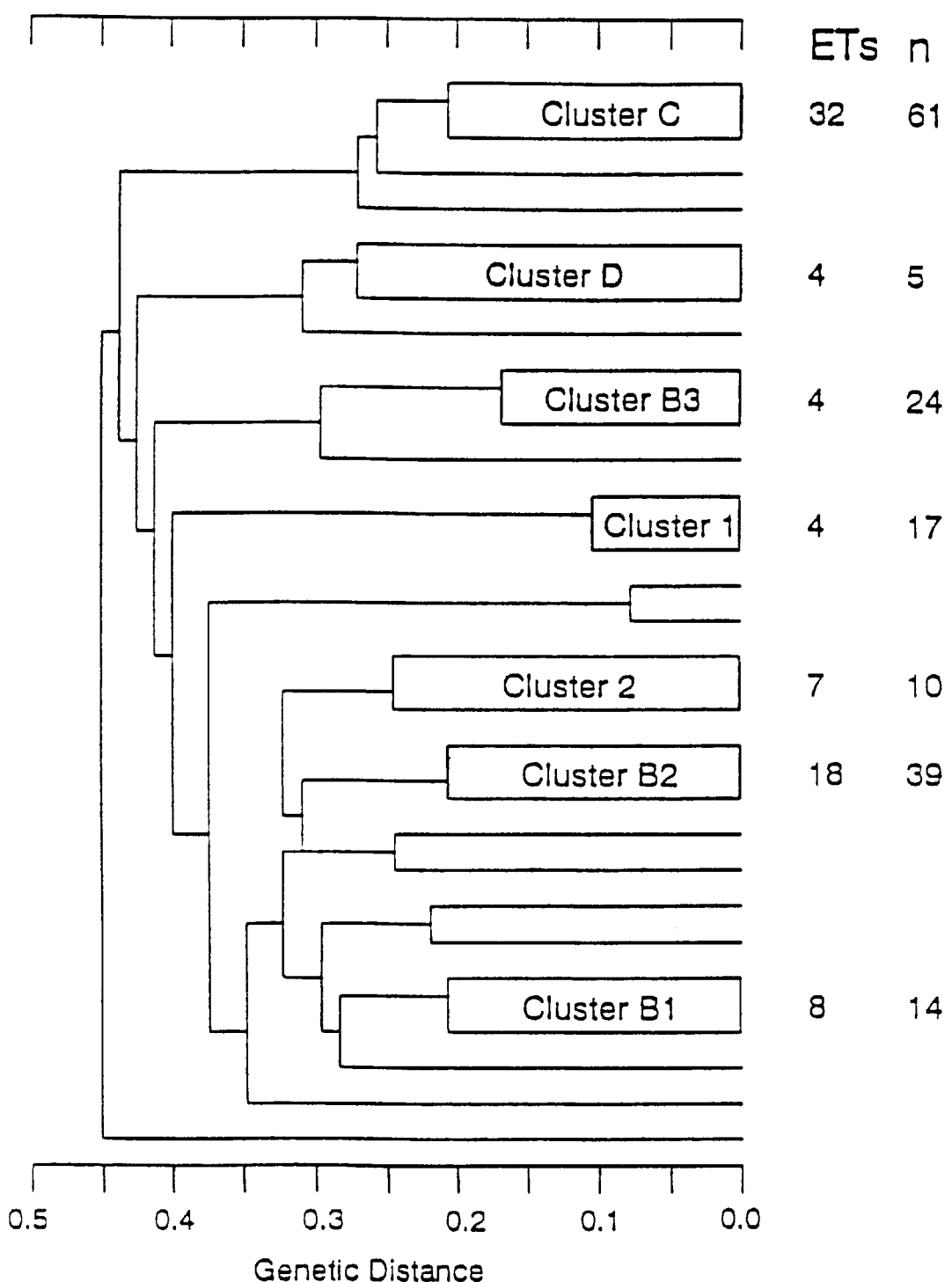
FIG. 1. Phylogenetic tree of 6 major clusters containing 19 clones selected for evaluation of pathogenicity. Genetic distance is based on the proportion of matches at 20 enzyme loci. The number of ETs and isolates represented by each major cluster is given in the columns on the right.

[a]Abbreviations: AS, airsacculitis; Sep, septicemia; N, not condemned
[b]Abbreviations: Out, from surface of organ; In, from within the organ The isolates were obtained from birds condemned due to airsacculitis (9 birds; 10 isolates) or septicemia (14 birds; 17 isolates), or not condemned (6 birds; 6 isolates) by USDA inspectors at the processing plants. Using aseptic precautions, swabs were obtained from within the mass and the surface of the liver and lung, directly plated on tergitol 7 agar, and incubated at 37° C. overnight. Multilocus enzyme electrophoresis and serotyping were performed as described previously [White, D. G., et al. *Infect. Immun.* 58:3613–3620, 1990]. *E. coli* strains representing 19 major clones containing 96 isolates out of a total of 188 were genetically analyzed by multilocus enzyme electrophoresis as described [Kapur, V. et al. Characterization and Clonal Analysis of *Escherichia coli* Isolated from Poultry During Processing, Manuscript in preparation]. Each of the isolates belonged to one of 6 major clusters (FIG. 1) as determined by ETCLUS program written for DOS computers by T. S. Whittam which utilizes the average linkage algorithm. Cluster designations B1, B2, B3, C, and D were determined after comparing these isolates to those that have been previously recovered from clinical cases of colibacillosis.

Challenge studies. All challenge studies were carried out in three-week-old male broiler chicks [Arp, L. H. *Avian Dis.* 24:808–815, 1989]. The chicks were received at one-day of age from a commercial hatchery and reared as per standard management practices in positive pressure isolators on a continuous lighting regimen with ad lib water and feed supply. Bacterial isolates were grown to a $A_{600nm}$ of 1.0 in veal infusion broth (VIB) and 0.1 ml of this culture inoculated into the wing vein of the broiler chickens. Birds were observed and signs of disease and mortality recorded for up to 5 days post-inoculation.

Determination of $LD_{50}$. Strains 289 (ET-2, pathogenic) and 364 (ET-2, non-pathogenic) were grown to an $A_{600nm}$ of 1.0 in VIB representing approximately $5 \times 10^8$ colony-forming units (CFU) per ml as determined by plate counts. A total of five three-week-old commercial male broiler chicks were each inoculated with $5 \times 10^2$ through $5 \times 10^7$ CFU of either strain and mortality recorded over a period of five days post-inoculation. $LD_{50}$ values were calculated as per the method of Reed and Muench [Villegas, P., et al. *A Laboratory Manual for the Isolation and Identification of Avian Pathogens*, 3rd ed. Purchase H. G., et al., eds., The American Association of Avian Pathologists, P. 186, 1989].

Antibiotic sensitivity patterns. The susceptibility of the bacterial isolates to a panel of 13 antibiotics (Table 2) was tested using the BBL Prompt™ inoculation system for use with the sensi-disc antimicrobial susceptibility test discs (BBL Microbiology systems, Cockeysville, Md.), and the results interpreted as per manufacturers instructions.

TABLE 2

Sensitivity a of 9 isolates of *E. coli* of ET-2 to 13 antibiotics[b]

| Antibiotic | Strain Number | | | | | | | | |
|---|---|---|---|---|---|---|---|---|---|
| | 270 | 289 | 291 | 306 | 309 | 313 | 323 | 364 | 417 |
| Ampicillin | S | S | S | S | S | S | S | S | S |
| Bacitracin | R | R | R | R | R | R | R | R | R |
| Cephalothin | R | R | R | R | R | R | R | R | R |
| Erythromycin | R | R | R | R | R | R | R | R | R |
| Furazolidone | I | R | R | I | R | R | R | S | I |
| Gentamycin | R | R | R | R | R | R | R | R | R |
| Kanamycin | R | I | I | I | I | I | R | R | R |
| Neomycin | R | I | I | I | I | I | I | R | R |
| Novobiocin | R | R | R | R | R | R | R | R | R |
| Penicillin | R | R | R | R | R | R | R | R | R |
| Spectinomycin | R | R | R | R | R | R | R | R | R |
| Sulfadimethoxine with Oremetoprim | S | S | S | S | S | S | S | I | I |
| Tetracycline | R | R | R | R | R | R | R | R | R |

[a]Abbreviations: R, resistant; I, intermediate; S, sensitive
[b]Interpretations by Bauer-Kirby method Isolation of Outer-Membrane Proteins. Outer-membrane proteins (OMPs) were isolated by the method described by Deneer and Potter [Deneer, H. G., et al. *J. Gen. Microbiol.* 135:435–443, 1989] with minor modification. Bacterial strains were grown overnight at 37° C. in 100 ml of Luria Broth and cells were recovered by centrifugation (6,000 G for 10 min at 4° C.), suspended in 3 ml of HEPES (Sigma Chemical Co., St. Louis, Mo.; 10 mM, pH 7.4), and disrupted by treatment with sonication (45 s at 50% output; Braunsonic). Cell debris was removed by centrifugation at 6,000 g for 10 min at 4° C. The supernatant was added to 0.75 ml of 2% N-Lauroylsarcosine (sarkosyl, Sigma Chemical Co., St. Louis, Mo.) and incubated for 10 min at room temperature. The mixture was centrifuged at 100,000 G for 1 h (Beckman 70.1 Ti, 39K) in order to recover the detergent solubilized outer-membrane proteins. The pelleted proteins were resuspended in 3 ml of 10 mM HEPES (pH 7.4), incubated in the presence of one volume of sarkosyl at room temperature for 20 min, recovered by ultracentrifugation as described above. The final pellet was resuspended in 1 ml of 10 mM HEPES and stored at −20° C. SDS-PAGE [Ausubel, F. M., et al. *Current protocols in molecular biology*, Greene publishing Associates and Wiley-Interscience, 1990] was carried out with a 4% stacking and 8% separating gel after solubilizing the OMP preps at 100° C. for 7 min in 0.05 M Tris-HCL buffer (2.5% SDS, 5% 2-mercaptoethanol, 25% glycerol, and 0.003% bromophenol blue). The gels were stained with Coomassie Brilliant blue R250 (Sigma Chemical Co., St. Louis, Mo.).

Plasmid analysis. Alkaline lysis mini preparations were made in order to isolate plasmids from these *E. coli* strains [Ausubel, F. M., et al. *Current protocols in molecular biology*, Greene publishing Associates and Wiley-Interscience, 1990]. In brief, *E. coli* were grown overnight at 37° C. in 10 ml of L-broth. The bacterial cells were recovered by centrifugation (5,000 G for 10 min at 4° C.) and resuspended in 600 μl of Tris-EDTA (TE) buffer (pH 8.0). A total of 200 μl of the suspension was aliquoted into microcentrifuge tubes to which 400 μl of NaOH-SDS lysis solution was added, mixed by gentle tapping, and placed on ice for 5 min. The lysis solution was neutralized by the addition of 300μl potassium acetate (pH 5.8), mixed thoroughly, and placed on ice for 5 min. The admixture containing lysed cells was then centrifuged in a microcentrifuge (13,500 G for Imin), the supernatant aliquoted to fresh microfuge tubes, and the DNA pelleted with two volumes of ethanol. The precipitated DNA was pelleted in a microcentrifuge (13,500 G for 1 min), the pellet washed with 70 percent ethanol, and dried under vacuum. The dried pellet was then resuspended in 20 μl TE buffer (pH 8.0) containing 10 μl of RNase. The plasmid DNA was resolved in 0.8% agarose gels in Tris-Borate-EDTA [TBE; Ausubel, F. M., et al. *Current protocols in molecular biology*, Greene publishing Associates and Wiley-Interscience, 1990], stained with ethidium bromide, and visualized and photographed over UV light.

Protection experiment 1. Strains 289, 364, or 82-0884 (serotype 02:K-:HN) were grown overnight at 37° C. in 100 ml of nutrient broth, centrifuged at 5,000 G for 10 min, and the pellet resuspended in 10 ml of normal saline (NS). The suspension was heated at 100° C. for 30 min, examined for sterility and mixed with equal quantities of Freund's incomplete adjuvant (Sigma Chemical Co., St. Louis Mo.) in order to prepare the heat-inactivated bacterins. Sixty male broiler chicks were procured and reared as described above. At three weeks of age, 15 chicks were inoculated intramuscularly either two (5 chicks) or three (5 chicks) times one week apart with 0.5 ml of either of the 3 bacterins containing approximately $2.5 \times 10^9$ cells nor normal saline. The chickens were challenged and observed for clinical signs and mortality as described above either two or three weeks after the initial vaccination.

Protection experiment 2. Experiment 2 was similar in design to that of experiment 1 except that the bacterial strains were grown overnight at 37° C. in 5 ml VIB, heat inactivated, and not mixed with adjuvant. The three-week-old male broiler chicks were inoculated intravenously with 0.1 ml of the heat-inactivated bacterin containing approximately $5 \times 10^7$ bacterial cells two or three times one week apart and challenged as in experiment 1.

Protection experiment 3. Experiment 3 was conducted in order to evaluate the efficacy of strain 364 as a live vaccine. When three days old, 34 male broiler chicks were inoculated subcutaneously with NS (5 chicks) or oil-adjuvant bacterins from strains 289 (12 chicks), 364 (8 chicks), or 82-0884 (9 chicks) prepared as in experiment 1. At three-weeks-of-age, 3 chicks from each of the groups primed with NS, strain 289, or strain 82-0884, and two chicks from the group primed with strain 364 were vaccinated with 0.1 ml of NS, and the balance of the chicks divided into vaccinal groups as follows: 4 chicks previously primed with strain 289 were intravenously inoculated with 0.1 ml of heat-inactivated strain 289 as prepared in experiment 2; 4 chicks previously primed with strain 82-0884 were intravenously inoculated with 0.1 ml of heat-inactivated strain 82-0884 as prepared in experiment 2; the remaining chicks from the NS (2), 289 (5), 364 (6), or 82-0884 (2) primed groups were intravenously administered untreated viable strain 364 containing approximately $5 \times 10^7$ bacterial cells. Each group was vaccinated three times, one week apart, and challenged with pathogenic strain 289 as described above.

Challenge studies. A total of 7 of the 19 strains representing commonly isolated clones from processing plants evaluated for ability to cause mortality by intravenous inoculation to three-week-old chicks were found to be pathogenic (Table 3).

TABLE 3

Pathogenicity of *E. coli* strains belonging to 19 major ETs representing 96 isolates recovered from processing plants

| Cluster | ET (n) | Isolate | Serotype[a] O:H | Mortality[b] (%) |
|---|---|---|---|---|
| 1 | 6(4) | 298 | 0117:HN | 0 |
|   | 15(8) | 331 | O23:NM | 33 |
|   | 46(4) | 436 | O37:NM | 0 |
| BT | 4(4) | 281 | ON:HN | 0 |
|   | 20(1) | 351 | ON:NM | 33 |
| B2 | 1(3) | 266 | O15:NM | 0 |
|   | 14(3) | 329 | ON:NM | 0 |
|   | 25(4) | 368 | ON:NM | 0 |
|   | 31(6) | 393 | ON:HN | 66 |
|   | 69(5) | 503 | O9:HN | 0 |
| B3 | 2(20) | 270 | ON:NM | 100 |
| C | 7(5) | 302 | ON:NM | 0 |
|   | 33(3) | 397 | O88:NM | 0 |
|   | 34(5) | 403 | O5:H10 | 0 |
|   | 41(2) | 418 | ON:NM | 66 |
|   | 54(6) | 463 | O15:H33 | 33 |
|   | 57(7) | 468 | O6:NM | 0 |
|   | 59(2) | 477 | x18:NM | 0 |
| D | 16(4) | 333 | O2:NM | 33 |

[a]Abbreviations: ON, O nontypeable; HN, H nontypeable; NM, non-motile.
[b]Each isolate was intravenously inoculated to 3 chicks.

Both pathogenic and non-pathogenic strains were isolated from each of the major clusters with the exception of clusters B3 and D from which the single strains examined were pathogenic. The largest cluster, both in terms of number of ETs and number of isolates, was cluster C. From a total of 32 ETs representing 61 isolates in this cluster, we examined strains from 7 ETs accounting for 30 (49%) of the isolates. Only 2 of the strains (418 and 463) representing 8 isolates were shown to be pathogenic whereas 5 strains (302, 397, 403, 468, and 477) did not cause mortality in three week-old chicks. The single largest clone in our sample from processing plants, Et-2 from cluster B3, consisting of a total of 20 isolates recovered from 10 different carcasses, was found to be pathogenic. This clone was identical to a O78: HN isolate recovered from a case of turkey colisepticemia in Minnesota (data not shown). In order to compare the pathogenicity of isolates belonging to the same major clone, as indicated by identity in electrophoretic type isolates from ET-2 in cluster B3 along with those of ETs 34, 54, and 59 of cluster C (Table 4) were examined.

TABLE 4

Comparison of pathogenicity of isolates within electrophoretic types (ETs) belonging to major clusters

| Cluster | ET | Isolate | Serotype O:H | Disease Class |
|---------|----|---------|--------------|---------------|
| B3 | 2 | 270 | ON:NM | Pathogenic |
|  |  | 289 | ON:NM | Pathogenic |
|  |  | 291 | ON:NM | Pathogenic |
|  |  | 306 | ON:NM | Pathogenic |
|  |  | 309 | ON:NM | Pathogenic |
|  |  | 313 | ON:NM | Pathogenic |
|  |  | 323 | ON:NM | Pathogenic |
|  |  | 364 | ON:NM | Non-pathogenic |
|  |  | 417 | ON:NM | Pathogenic |
| C | 34 | 403 | O5:NM | Non-pathogenic |
|  |  | 433 | O6:H10 | Non-pathogenic |
|  |  | 475 | O126:HN | Non-pathogenic |
|  | 54 | 463 | O15:H33 | Pathogenic |
|  |  | 470 | O76-NM | Non-pathogenic |
|  |  | 478 | ON:NM | Non-pathogenic |
|  |  | 489 | ON:NM | Non-pathogenic |
|  | 59 | 464 | x18:NM | Non-pathogenic |
|  |  | 477 | x18:NM | Non-pathogenic |

Abbreviations: ON, O nontypeable; HN, H nontypeable; NM, non-motile

Of the 9 isolates examined for pathogenicity in ET-2, 8 were pathogenic with the only non-pathogenic isolate being strain 364 which was recovered from the liver of a bird condemned for airsacculitis. From cluster C, we examined 3 isolates from ET-34 all of which were found to be pathogenic. In ET-54, strain 463 was confirmed to be pathogenic as observed in the previous trial. However, the other strains in this ET (470, 478, and 479) did not cause mortality in three-week-old chicks. Of the two isolates examined from ET-59, both were found to be non-pathogenic. Thus, with only the two exceptions of strains 364 from ET-2 and 463 from ET-54 isolates from within an ET were all either pathogenic or non-pathogenic.

Phenotypic variation among pathogens and non-pathogens. In order to determine the reason for differences in pathogenicity of strains within the same ET, isolates were chosen from ET-2 as this was the single largest clone in our sample matched up exactly with an isolate previously recovered from turkey colisepticemia, and had a single non-pathogen among 9 isolates recovered.

When comparing the pathogenic strain 289 with the non-pathogen 364 for mean lethal dose, the $LD_{50}$ of strain 289 was determined to be $5.3 \times 10^{5.8}$ CFU. The mean lethal dose for strain 364 could not be calculated as only one bird from the group inoculated with $5 \times 10^7$ died. However, the birds inoculated with 0.1 μl of undiluted strain 364 did not appear to be as thrifty or put on as much weight as control birds upon termination of the experiment at day 5 post-inoculation (data not shown). Despite the apparent signs of chronic colibacillosis, no E coli could be recovered from the heart blood or liver.

Figure 2:
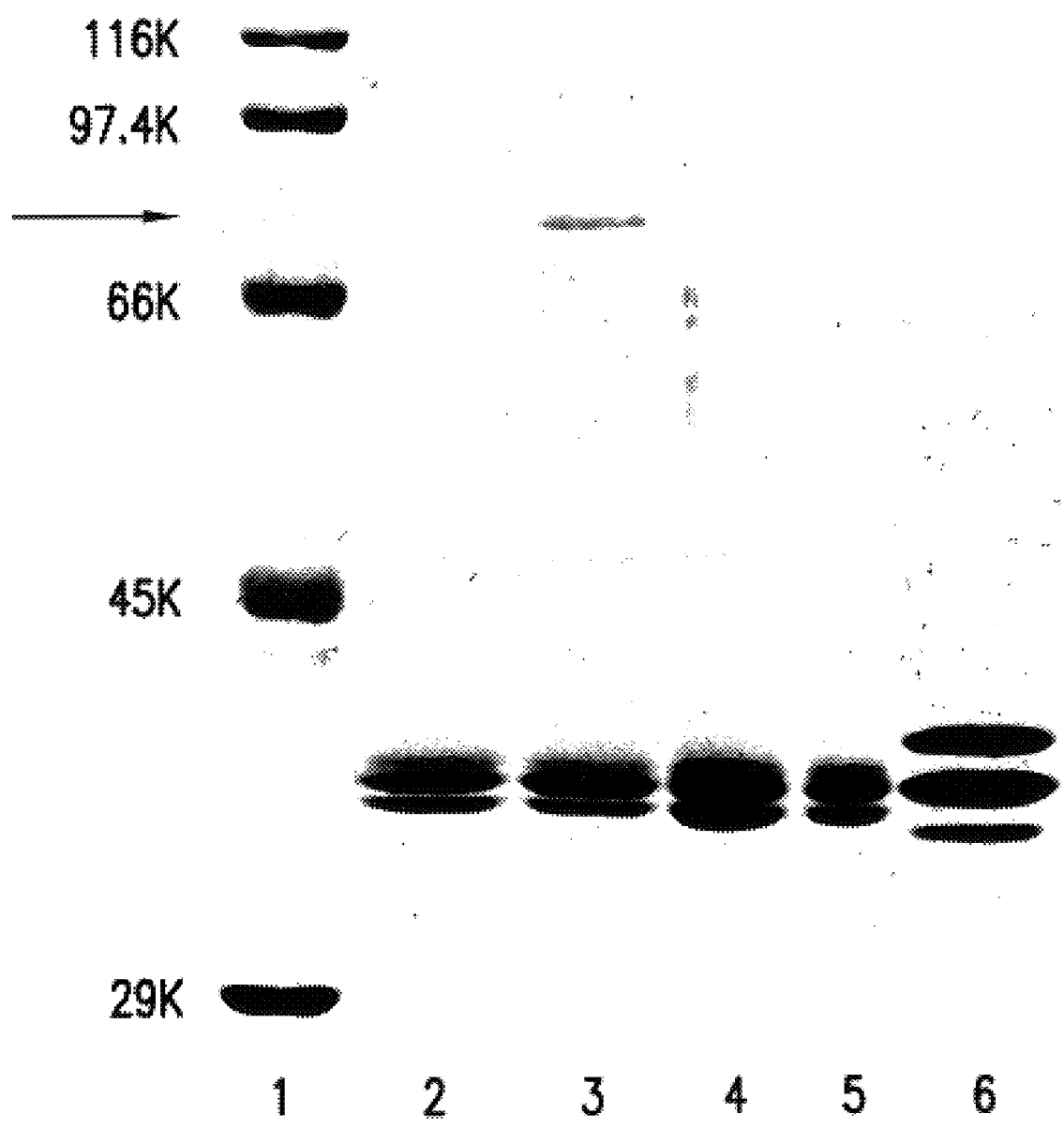
FIG. 2. Comparison of major outer membrane proteins (OMPs) between pathogenic strain 289 and non-pathogenic isolate 364. The molecular weights of protein standards in lane 1 are indicated in the left column in kilodaltons (K). Lanes 2 through 6 contain the following OMP preparations from the following isolates: 289 first preparation; 364 first preparation; 289; 364; 82-0884.

The sensitivity patterns of 9 isolates from ET-2 to a panel of 13 antibiotics are given in Table 2. The only major difference between the non-pathogenic strain 364 and the other 8 pathogenic ones was in susceptibility to furazolidone (Table 2). The other isolates in this clone were either resistant (strains 289, 291, 309, 313, and 323) or intermediate (strains 270, 306, and 417). However, strain 364, like 270 and 417, was resistant to both kanamycin and neomycin whereas the rest were intermediate in resisting the effects of the antibiotic. No differences in migration patterns of the major OMPs were noted for any of the 9 isolates examined from this clone. The isolates all had a similar banding pattern in which three major bands, probably representing a porin, K protein, and OMP A, were visualized [Achtman, M., et al. Infect. Immun. 39:315–335, 1983]. The banding patterns for the strains 289 and 364 are shown in FIG. 2 Lanes 3 and 4). Interestingly, during one particular batch of OMP preparation, a high molecular weight band of approx 75 KDa, not corresponding to any of the major OMPs was seen in strain 364 (lane 3, arrow). This band was not subsequently observed in any of several other preparations made from the same strains. The presence of this band is interesting as it may represent a stress related protein. On the other hand, it may be an artifact acquired during preparation of the OMP fractions.

Figure 3:
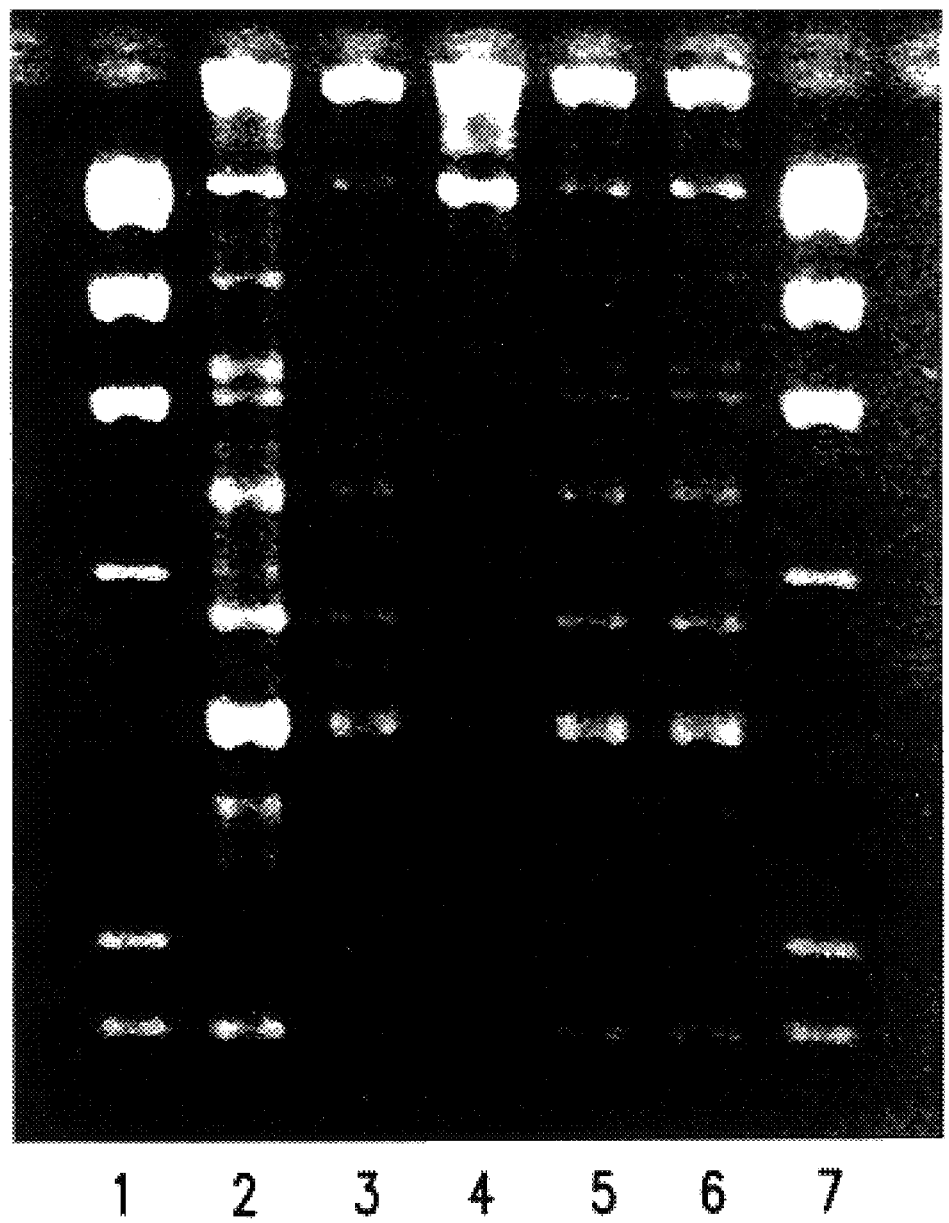
FIG. 3. Plasmid profiles of selected isolates from ET-2. Lanes 1 and 7 contain lamda HindIII digest with molecular weight (MDa) indicated in the left column. Lanes 2, 3, 5 and 6 contain plasmid preparations from pathogenic isolates 289, 309, 312 and 291 respectively. Plasmid preparation from non-pathogenic strain 364 is in lane 4.

Analysis of plasmid profiles of the pathogenic strains 289, 291, 309, and 312 along with that of non-pathogenic strain 364 revealed some interesting differences (FIG. 3). Each of the pathogenic isolates had several plasmids varying from over 15 to around 1.34 MDa (Lanes 2, 3, 5 and 6) while the non-pathogenic isolate had only a single plasmid of approximately 15 MDa size (lane 4). This difference is even more intriguing as there were no such differences observed in antibiotic sensitivity profiles. These results are repeatable even when using a commercial plasmid isolation and purification kit (Qiagen Inc, Chatsworth, Calif.) using anion-exchange columns with modified silicagel to reduce non-specific binding.

Evaluation of cross-protection. Preliminary trials were conducted for evaluating the use of heat-inactivated oil-adjuvant bacterin prepared by heating E. coli strains 289, 364, or 82-0884 (serotype O2:K-:HN) in male broiler chicks. No significant cross-protection was obtained between strain 364 and 289 (data not shown). Similarly, no cross-protective effects of heat-inactivated bacterin containing approximately 5×1 bacterial cells given intravenously were noted.

The results from experiment 3 of the cross-protection study revealed that strain 364, when administered intravenously as an unmodified culture, was significantly protective against challenge with pathogenic strain 289 (Table 5).

TABLE 5

Mortality after intravenous challenge with E. coli strain 289 in male broiler chickens after immunization with homologous and heterologous strains

| | | | Mortality (days post-challenge) | | | | | | | Total | |
|---|---|---|---|---|---|---|---|---|---|---|---|
| Group | Prime | $n^a$ | 1 | 2 | 3 | 4 | 5 | Total | (%) | Total Group | (%) |
| NS | NS | 3 |  | 1 | 1 |  | 1 | 3 | (100) | 8/11 | (72.7) |
|  | 289 | 3 |  | 2 |  |  |  | 2 | (66) |  |  |

TABLE 5-continued

Mortality after intravenous challenge with *E. coli* strain 289 in male broiler chickens after immunization with homologous and heterologous strains

| Group | Prime | n[a] | 1 | 2 | 3 | 4 | 5 | Total | (%) | Total Group | (%) |
|---|---|---|---|---|---|---|---|---|---|---|---|
|  | 364 | 2 |  | 2 |  |  |  | 1 | (50) |  |  |
|  | O2 | 3 |  | 1 | 1 |  |  | 2 | (66) |  |  |
| 289 | 289 | 4 |  |  | 1 |  |  | 1 | (25) | 1/4 | (25) |
| 364 | NS | 2 |  |  |  |  |  | 0 | (0) | 2/15 | (13.3) |
|  | 289 | 5 |  |  |  |  |  | 0 | (0) |  |  |
|  | 364 | 6 | 1 |  |  |  |  | 1 | (17) |  |  |
|  | O2 | 2 |  |  | 1 |  |  | 1 | (50) |  |  |
| O2 | O2 | 4 | 1 | 2 | 1 |  |  | 4 | (100) | 4/4 | (100) |

[a]Number of chickens

While 73 percent of the birds in the control group died, the mortality upon challenge was only 13.3% in the group administered live non-pathogenic strain 364 (G=9.98, P=0.002).

DISCUSSION

It is interesting to note that isolates from cluster C, the largest cluster in this study with the most number of ETs and isolates have been previously characterized as frequently being associated with apparently healthy birds, were less pathogenic and had a lower percentage of aerobactin producing strains than other clusters. The results from this study also show that the cluster C intended to have fewer pathogenic ETs than other clusters. Isolates representing major clones from cluster B1 and B2, whose isolates were found to be of high to moderate pathogenicity were found to be associated with few pathogenic clones in this study. A majority of the isolates from cluster B3 were pathogenic. These results are in agreement with those of White et al. (1991) who found that 67% of the isolates from this cluster were highly pathogenic, produced aerobactin, and more frequently recovered from the heart and air sac than any other tissue. The theory that pathogenic bacteria have a clonal structure, stems from studies with various pathogens such as *E. coli* [Whittam, T. S., et al. *Infect. Immun.* 56:2458–2466, 1988; White, D. G., et al *Infect. Immun.* 58:3613–3620, 1990], *Hemophilus influenzae* type b [Musser, J. M., et al. *Proc. Nat. Acad. Sci.* 82:5078–5082, 1985], *Staphylococcus aureus* [Musser, J. M., et al. *Proc. Nat. Acad. Sci.* 87:225–229, 1990], *Streptococcus pyogenes* [Musser, J. M., et al. *Proc. Nat. Acad. Sci.* 88:2668–2672, 1991], and *Mycobacterium avium* complex [Wasem C. F., et al. *J. Clin. Microbiol.* 29:264–271, 1991] among others. These studies have demonstrated the clonal nature of pathogenic bacteria based on electrophoretic analysis of isolates recovered from various disease syndromes. However, none of these reports have evaluated isolates from within a clone in their ability to cause disease and mortality by experimental inoculation of the putative pathogens. Our analysis of major clones from processing plants clearly demonstrates that isolates from within a clone, with few exceptions, are uniform in their ability to cause disease. These results lend further support to the clonal hypothesis for bacterial populations [Selander, R. K., et al. *Microbial Pathogenesis* 3:1–7, 1987].

The presence of a single non-pathogenic isolate in a pathogenic clone was intriguing. The antibiotic sensitivity patterns were similar among all the isolates with the exception of susceptibility to furazolidone for the non-pathogenic isolate 364. The absence of a majority of the plasmids in the non-pathogenic strain was especially interesting as this strain was resistant to 11 of 13 antimicrobial agents to which resistance is frequently plasmid associated. The role of the plasmids in ability of these pathogenic strains to cause disease warrants further investigation.

The role of OMPs in pathogenicity and host-pathogen interactions has been the focus of recent attention for several pathogens including *E. coli* [Chanyangarn, M., et al. *Infect. Immun.* 59:600–608, 1991; Robledo, J. A., et al. *J. Urol.* 143:386–391, 1990; Sherman, P., et al. *Infect. Immun.* 59:890–899, 1991; Weiser, J N., et al. *Infect. Immun.* 59:2252–2258, 1991]. In addition, the role of a porin as contributing to susceptibility to antibiotics has also been proposed [Toro, C. S., et al. *Antimicrob. Agents Chemotherap.* 34:1715–1719, 1990]. In this study, no differences in major OMP patterns was apparent among the members of clone ET-2 from cluster B3. However, as the growth medium and conditions of growth have a major impact on the expressions of OMPs [Achtman, M., et al. *Infect. Immun.* 39:315–335, 1983], the possibility that the absence or presence of certain OMPs in vivo plays a role in susceptibility of strain 364 to the hosts defense mechanisms cannot be ruled out since the bacteria were grown in artificial media during this study. The presence of the high molecular band in the non-pathogenic isolate in one of our OMP preparations is intriguing. Proteins of this molecular weight are usually porins which are known to play an important role in transport of nutrients into the cells, and whose expression is determined by the environment. However, the absence of any repeatable difference in the major OMP pattern was useful as it afforded us the opportunity to successfully exploit any immunogenic properties of these proteins in order to use non-pathogenic strains to protect against pathogenic ones as is evidenced from Table 5.

The inability of heat-inactivated bacterins to protect against disease due to heterologous challenge was not altogether unexpected as these have been previously reported to provide unsatisfactory immunity to challenge with homologous strains [Deb., J. R., et al. *Res. Vet. Sci.* 20:131–138, 1976]. However, unlike results from the previous studies, we were able to elicit a significant immunity against challenge with a homologous strain by vaccinating intravenously (Table 5). Subsequently, we used the inability of strain 364 to cause mortality in chickens when intravenously inoculated to protect against challenge with a pathogenic member of the same clone.

There are several reports in the literature on the preparation of vaccines against *E. coli* strains associated with avian colibacillosis [Rosenberger, J. K. *Vineland Update No.* 4: Vineland Laboratories, Vineland, N.J., 1983; Goren, E. *Avian Pathol.* 7:213–224, 1978; Deb., J. R., et al. *Res. Vet. Sci.* 20:131–138, 1976; Rosenberger, J. K., et al. Avian Dis. 29:1108–1117, 1986; Gyimah, J. E., et al. *Avian Dis.* 29:1078–1083, 1985;. Gyimah, J. E., et al. *Avian Dis.* 29:540–545, 1985; Gyimah, J. E., et al. *Avian Dis.* 30:687–689, 1986; Deb, J. R., et al. *Res. Vet. Sci.* 24:308–313, 1978; Heller, E. D., et al. *Avian Pathol.* 19:345–354, 1990; Leitner, G., et al. *Avian Dis.* 34:58–62, 1990; Melamed, D., et al. *Avian Dis.* 35:17–22, 1991; Arp, L. H. *Avian Dis.* 24:808–815, 1980; Panigrahy, B., et al. *Avian Dis.* 28:475–481, 1984; Peleg, B. A., et al. *Avian Pathol.* 14:471–481, 1985].

In addition, a commercial multivalent oil-emulsion bacterin has also been produced [Rosenberger, J. K. *Vineland Update No.* 4: Vineland Laboratories, Vineland, N.J., 1983]. All of these reports have described the preparation of vaccines based on the fact that a majority of the isolates that are recovered from clinically ailing birds belong to a relatively few serotypes without taking into consideration the genetic structure of *E. coli* populations. The results of previous attempts at controlling *E. coli* infections by vaccination have not been very successful or universally accepted. This finding might be partly due to the fact that serotyping may not be the appropriate attribute to consider for selection of vaccine strains. As has been shown by several workers [Whittam, T. S., et al. *Infect. Immun.* 56:2458–2466,1988; White, D. G., et al. *Infect. Immun.* 58:3613–3620, 1990], organisms possessing the same serotype can be genetically diverse. Conversely, organisms with the same genetic background may possess different somatic and flagellar antigens. This makes assumptions of clonality based upon common serogroups among avian strains of *E. coli* problematic. In addition, a vast majority of avian strains of *E. coli* cannot be classified using presently available antisera, thereby increasing the potential of not recognizing major bacterial clones in avian populations when using serotype or biotype data alone. Thus, the need for evaluating the efficacy of closely related isolates to elicit protective immune response is critical. This will afford optimal selection of bacterial strains in order to maximize immune response to the widest spectrum of organisms by choosing strains belonging to the most commonly isolated genotypes as well as sharing phenotypic attributes such as serotype.

This represents the first report to use the clonal structure of bacterial populations in order to successfully vaccinate against pathogenic organisms by selecting out closely related non-pathogenic organisms.

Live *E. coli* isolates of the invention, or combinations or variants thereof, capable of effecting poultry immunization, may be administered in any pharmaceutically-acceptable fashion in such concentrations as shall be necessary to produce appropriate immunity.

Thus is described our invention and the manner and process of making and using it in such full, clear, concise, and exact terms so as to enable any person skilled in the art to which it pertains, or with which it pertains, or with which it is most nearly connected, to make and use the same.

What is claimed is:

1. A method for identifying a protective bacterial immunogen, comprising:
    (a) collecting bacterial isolates;
    (b) genotyping said bacterial isolates;
    (c) selecting naturally occurring bacterial isolates that are non-pathogenic from a genotypic class that includes pathogenic bacteria; and
    (d) screening said selected naturally occurring non-pathogenic bacterial isolates for protective immunogenicity against said pathogenic bacteria.

2. The method according to claim 1, wherein said genotyping is accomplished by multilocus enzyme electrophoresis.

3. The method according to claim 1, wherein said bacterial immunogen is *E. coli* strain 364.

4. The method according to claim 1, wherein said bacterial isolates are collected from poultry.

5. The method according to claim 4, wherein said poultry are chicken.

6. The method of claim 1 wherein the collecting is from diseased and healthy animals.

7. The method of claim 1 wherein the bacterial isolates are *Escherichia coli*.

* * * * *